(12) United States Patent
Kang et al.

(10) Patent No.: US 8,852,655 B2
(45) Date of Patent: Oct. 7, 2014

(54) ANTI-INFLAMMATORY AND ANTIOXIDANT COSMETIC COMPOSITION CONTAINING GREEN TEA POLYSACCHARIDE AND TRICHOLOMA MATSUTAKE EXTRACT

(75) Inventors: Chan Koo Kang, Seoul (KR); Sung A Cho, Anyang-si (KR); Ji Hyun Kim, Yongin-si (KR); Hui Kyoung Chang, Yongin-si (KR); Nok Hyun Park, Seoul (KR); Jun Cheol Cho, Suwon-si (KR)

(73) Assignee: Amorepacific Corporation, Seoul (KR)

( * ) Notice: Subject to any disclaimer, the term of this patent is extended or adjusted under 35 U.S.C. 154(b) by 614 days.

(21) Appl. No.: 12/700,074

(22) Filed: Feb. 4, 2010

(65) Prior Publication Data

US 2011/0097356 A1 Apr. 28, 2011

(30) Foreign Application Priority Data

Oct. 27, 2009 (KR) .............................. 2009-0102325

(51) Int. Cl.
- *A61K 36/00* (2006.01)
- *A61K 36/82* (2006.01)
- *A61K 8/73* (2006.01)
- *A61Q 19/08* (2006.01)
- *A61K 8/97* (2006.01)
- *A61K 36/07* (2006.01)

(52) U.S. Cl.
CPC . *A61K 36/07* (2013.01); *A61K 8/73* (2013.01); *A61Q 19/08* (2013.01); *A61K 8/97* (2013.01); *A61K 36/82* (2013.01)
USPC .......................................... 424/729; 424/725

(58) Field of Classification Search
None
See application file for complete search history.

(56) References Cited

U.S. PATENT DOCUMENTS

2008/0113044 A1* 5/2008 Alberte et al. ............... 424/729

FOREIGN PATENT DOCUMENTS

| JP | 2007320870 A | * 12/2007 |
| KR | 1020030032631 A | 4/2003 |
| KR | 100700912 B1 | 3/2007 |

OTHER PUBLICATIONS

Notice of Preliminary Rejection (and English translation) in Korean application 10-2009-0102325 mailed May 2, 2011.

* cited by examiner

*Primary Examiner* — Qiuwen Mi
(74) *Attorney, Agent, or Firm* — Nixon & Vanderhye P.C.

(57) ABSTRACT

Disclosed herein is a cosmetic composition which can inhibit skin aging resulting from external harmful environmental factors such as UV light and environmental pollution, which promote aging. More specifically, disclosed is a cosmetic composition, which contains green tea polysaccharide and *Tricholoma matsutake* extract and shows an excellent anti-aging effect by inhibiting skin inflammatory and oxidative processes.

12 Claims, 1 Drawing Sheet

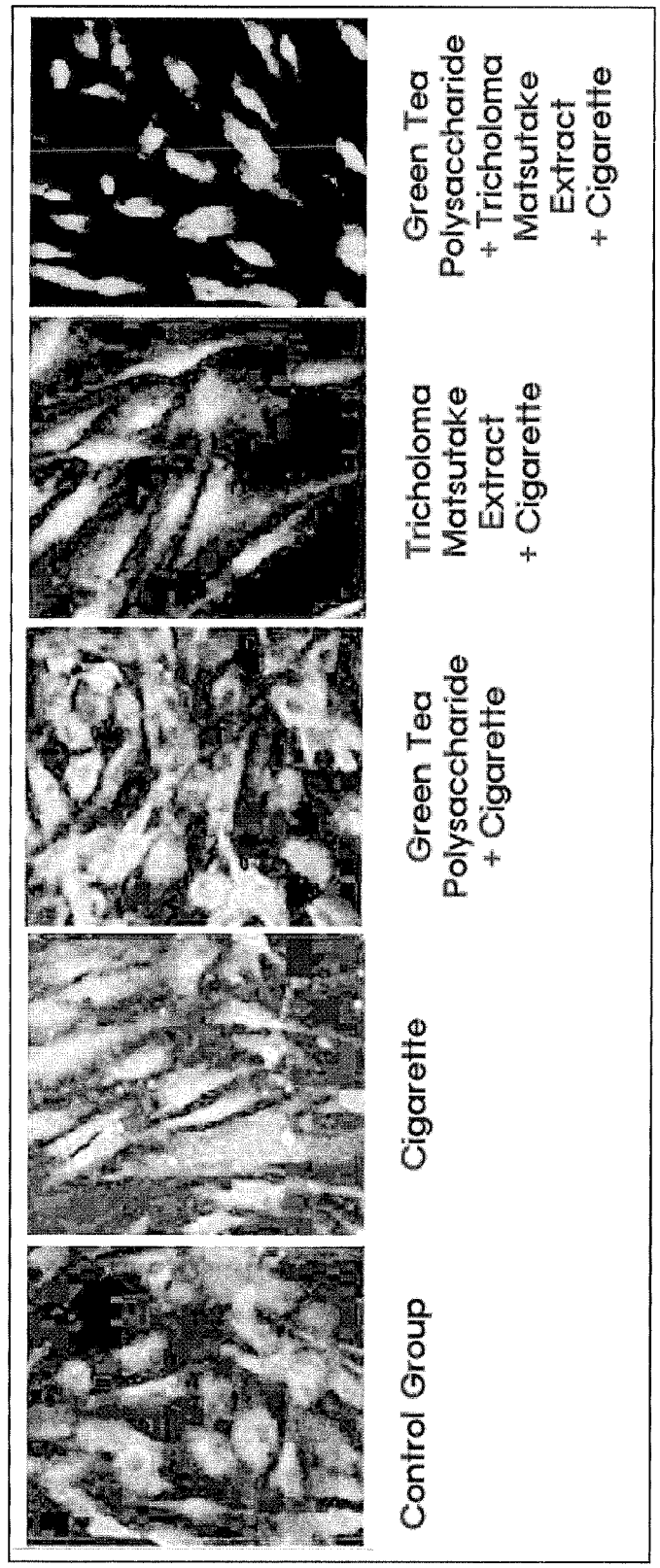

ANTI-INFLAMMATORY AND ANTIOXIDANT COSMETIC COMPOSITION CONTAINING GREEN TEA POLYSACCHARIDE AND TRICHOLOMA MATSUTAKE EXTRACT

CROSS-REFERENCE TO RELATED APPLICATIONS

This application claims the benefit of Korean Patent Application No. 10-2009-102325, filed on Oct. 27, 2009 in the Korean Intellectual Property Office, which is incorporated herein by reference in its entirety.

BACKGROUND OF THE INVENTION (a) Field of the Invention

The present invention relates to a cosmetic composition which can inhibit skin aging resulting from external harmful environmental factors such as UV light and environmental pollution, which promote aging. More specifically, the present invention relates to a cosmetic composition, which contains green tea polysaccharide and *Tricholoma matsutake* extract and shows an excellent anti-aging effect by inhibiting skin inflammatory and oxidative processes.

(b) Background of the Related Art

Generally, cosmetic products aim to make the body clean, make one's appearance beautiful and attractive and protect the skin or hair from UV light or drought to prevent aging. Recently, as the desire to express oneself is increasing with the development of industrial society and the increase of social activity, the desire to keep one's skin beautiful and healthy using cosmetic products is greatly increasing. Moreover, interest in environmental problems, such as global warming caused by rapid industrialization, air pollution and water pollution, is also increasing. For reference, the Intergovernmental Panel on Climate Change (IPCC) reported that the earth's surface temperature has increased by about 0.65° C.; over the past 50 years and that ozone depletion and global warming caused by greenhouse effect are serious. This indicates that air pollution is rapidly increasing.

Women of today who are active outdoors due to their active participation in life are being increasingly influenced by pollution as an external harmful environmental factor. Furthermore, the skin acting as a barrier against this external harmful environmental factor pollution is also being increasingly damaged and aged. Recent study results indicate that external pollutants such as ozone, carbon dioxide, carbon monoxide, formaldehyde, environmental hormones and cigarette smoke promote skin aging. More specifically, ozone can retard cell proliferation and induce lipid peroxidation, carbon dioxide can induce skin itching, cigarette smoke can induce skin inflammation, formaldehyde can induce allergy and eruption, and environmental hormones can induce pigmentation and eruption. Very importantly, such skin troubles are considered to promote wrinkle formation, make the skin tone dark and reduce skin elasticity, thus promoting skin aging.

The consumer's desire to look younger and to slow down aging and the expectation of the effects of cosmetic products are increasing, but cosmetic products which scientifically cope with such external harmful environmental factors and inhibit skin damage are rare in the market. Most anti-aging cosmetic products are for women older than 40 years whose skin has been significantly aged, and the relevant ingredients are focused on skin moisturization, skin elasticity improvement, wrinkle reduction and the like. In addition, the anti-aging ingredients are mostly synthetic products such as retinols or vitamins. In other words, it is considered that cosmetic products utilizing a combination of plant ingredients to alleviate skin damage caused by pollution have not yet appeared in the market.

SUMMARY OF THE INVENTION

Accordingly, the present inventors have conducted many studies to develop a combination of plant extracts, which can actively cope with the attack of external harmful environmental factors and can protect the skin from the external harmful environmental factors, and, as a result, have found that a combination of green tea polysaccharide and *Tricholoma matsutake* extract inhibits skin inflammation and skin oxidation to maximally retard skin aging, thereby completing the present invention.

It is therefore an object of the present invention to a cosmetic composition containing natural plant ingredients which are safe for the skin and, at the same time, show an excellent anti-aging effect by inhibiting skin inflammatory and oxidative processes.

To achieve the above object, the present invention provides a cosmetic composition containing, as active ingredients, green tea polysaccharide and *Tricholoma matsutake* extract.

The present inventors prepared an oil-in-water emulsion formulation and a soluble gel formulation using green tea polysaccharide and *Tricholoma matsutake* extract and examined the anti-inflammatory and anti-aging effects of the formulations. As a result, it could be found that these formulations could inhibit skin inflammatory and oxidative processes to keep the skin young. Also, the present invention can provide a cosmetic composition which shows the synergistic effects of green tea polysaccharide and *Tricholoma matsutake* extract, and thus shows an excellent effect of promoting the health of skin tissue acting as a direct barrier against external harmful environments by strongly inhibiting the expression of a pollution antenna which is activated by the external harmful environments.

BRIEF DESCRIPTION OF THE DRAWINGS

The above and other objects, features and advantages of the present invention will be apparent from the following detailed description of the preferred embodiments of the invention in conjunction with the accompanying drawings, in which:

FIG. 1 is a set of photographs showing the inhibitory effects of green tea polysaccharide and *Tricholoma matsutake* extract according to the present invention on the expression of an air antenna protein, which is caused by automobile exhaust gas.

DETAILED DESCRIPTION OF THE PREFERRED EMBODIMENT

Hereinafter, the present invention will be described in further detail.

The present invention provides a cosmetic composition containing, as active ingredients, green tea polysaccharide and *Tricholoma matsutake* extract.

Green tea polysaccharide which is used as an active ingredient in the present invention is derived from green tea (*Camellia sinensis*). It has not received less attention than green tea catechin in the past, but has recently received a great deal of attention. It is a group of acidic polysaccharides, unlike polysaccharides found in other plants, and is produced by binding of sugar components, made by photosynthesis, with amino acids. The green tea polysaccharide has the effects of inhibiting inflammation, which can occur due to external harmful environments, and relieving stimuli.

The green tea polysaccharide of the present invention can be obtained by any conventional method known in the art, and the method is not particularly limited. In a specific embodiment, green tea polysaccharide can be obtained by extracting green tea leaves with hot water at 80-90° C., concentrating the extract, filtering the concentrate to remove impurities, adding ethanol to the filtrate in a dropwise manner, and drying the ethanol solution in hot air.

The *Tricholoma matsutake* extract which is used as an active ingredient in the present invention is known to contain vitamins, minerals, amino acids and sugar components, as well as the antioxidant component Ergosterol which is found only in *Tricholoma matsutake*. Such active ingredients enhance skin resistance to external factors. The cosmetic composition according to the present invention utilizes a component extracted from *Tricholoma matsutake* grown in Korea, which is known to have the highest quality among *Tricholoma matsutake* grown all over the world, to inhibit skin oxidation resulting from pollution.

The *Tricholoma matsutake* extract according to the present invention can be obtained according to any conventional method known in the art, and the method is not particularly limited. In a specific embodiment, the *Tricholoma matsutake* extract can be obtained by extracting water-soluble components from *Tricholoma matsutake* with purified water at room temperature, adding ethanol to the extract to extract oil-soluble components, incubating for 3 days, and filtering the resulting material through a sterile filter.

Each of the green tea polysaccharide and *Tricholoma matsutake* extract of the present invention is contained in an amount of 0.01-20.0 wt %, and more preferably 0.1-10.0 wt %, based on the total weight of the composition. If the content of each of green tea polysaccharide and *Tricholoma matsutake* extract is less than 0.01 wt %, the desired effects cannot be obtained, and if the content exceeds 20.0 wt %, changes in the properties of cosmetic products, such as a change in smell, can occur. Also, in this case, it will not be easy to control the viscosity of cosmetic formulations, and phase conversion is likely to occur during the preparation of emulsion formulations, thus making it difficult to develop cosmetic formulations. In addition, productivity and cost-effectiveness will be reduced.

The mixing ratio of green tea polysaccharide to *Tricholoma matsutake* extract in the cosmetic composition of the present invention is 1.0:10.0 to 100:1.0. If the mixing ratio is out of the specified range, the synergistic effects of the two components cannot be obtained.

The progression of skin aging caused by harmful environments is accompanied by both inflammatory reaction and oxidative reaction, and if the two reactions are not simultaneously inhibited, it will be difficult to exhibit a strong anti-aging effect. For this reason, the green tea polysaccharide and the *Tricholoma matsutake* extract are preferably mixed at the above-described ratio.

In the present invention, the green tea polysaccharide and the *Tricholoma matsutake* extract are mixed with each other to prepare a future response complex. The future response complex is a combination of plant extracts, which early blocks the diffusion of skin aging signs by inhibiting the expression of a pollution antenna which is activated when various pollution factors transmit a harmful signal into the skin, and it targets arylhydrocarbon receptor (AhR) present in keratinocytes. It is known that this receptor is activated by environmental hormones, cigarette smoke, ozone and UV light, and after activation, it increases skin inflammatory factors and melanin, thus promoting skin aging.

The future response complex according to the present invention is a combination of plant extracts based on the results of scientific research conducted on the skin. If the green tea polysaccharide and the *Tricholoma matsutake* extract are used in combination, they will show synergistic effects and can retard the appearance of skin aging signs resulting from external harmful environments by effectively protecting the skin from damage caused by cigarette smoke, exhaust gas and the like.

The cosmetic composition of the present invention may be used in skin anti aging cosmetic products, and the formulation thereof is particularly limited. For example, the inventive composition can be formulated in the form of skin lotion, milk lotion, massage cream, nourishing cream, pack, gel or skin adhesive type cosmetic formulations, or transdermal formulations.

Furthermore, the cosmetic composition of the present invention may optionally contain, in addition to the above-described active ingredients, other additives which are conventionally added in cosmetic compositions. Examples of the additives include fat and oil components, moisturizers, emollients, surfactants, organic and inorganic pigments, organic powders, ultraviolet absorbents, preservatives, disinfectants, antioxidants, plant extracts, pH regulators, alcohols, pigments, perfumes, blood-circulation promoters, refrigerants, antiperspirants and purified water.

Hereinafter, the present invention will be described in further detail with reference to examples and test examples. It is to be understood, however, that these examples are for illustrative purposes only and are not to be construed to limit the scope of the present invention.

Test Example 1

Effects of Green Tea Polysaccharide and *Tricholoma matsutake* Extract on Inhibition of Reactive Oxygen Species Induced by Cigarette 1-1: Preparation of Cigarette Sample Cigarette butts after smoking were collected, and portions other than the filter portion were removed. Then, DMSO was added to the remaining filters in an amount of 1 ml/filter, and the filters were extracted using a shaker for 13 hours. The resulting sample was agitated in a vortexer for 10 minutes, followed by removal of the filters. The remaining material was centrifuged at 300 rpm for 5 minutes to remove the precipitate, thus obtaining a cigarette sample.

1-2: Measurement of Amount of Reactive Oxygen Species Generated in Cells

HaCaT cells were seeded into DMEM medium (containing 5% fetal bovine serum (FBS) and 100 IU penicillin G) in an S-well chamber slide at a density of 5,000 cells/well. The next day, each well was treated with one or both of 50 ppm of green tea polysaccharide (Bioland, Korea) and 100 ppm of *Tricholoma matsutake* extract (Bioland, Korea) for 24 hours. For a control group, each well was treated with DMSO alone at a concentration of $\frac{1}{1000}$, which was the same as the concentration of DMSO used to treat each well with the green tea polysaccharide and the *Tricholoma matsutake* extract. Then, 250 ppm of the cigarette sample was added to each of the media and incubated for additional 3 hours. Then, each well was washed twice with PBS, reacted with CFda at 37° C. for 20 minutes, and washed again with HESS. Each well was replaced with FBS-free and phenol red-free DMEM medium, and after 2 hours, an amount of reactive oxygen species generated in the cells was measured with a fluorometer. The measurement results are shown in Table 1 below.

TABLE 1

| Samples | Ratio of Reactive Oxygen Species(%) |
|---|---|
| Control Group | 100 |
| Cigarette | 165 |
| Green Tea Polysaccharide + Cigarette | 50 |
| Tricholoma Matsutake Extract + Cigarette | 77 |
| Green Tea Polysaccharide + Tricholoma Matsutake Extract + Cigarette | 22 |

As can be seen from the results in Table 1 above, in the group treated with the cigarette sample, the level of reactive oxygen species induced by the cigarette sample was increased to 165%, and in the groups treated with each of the green tea polysaccharide and the Tricholoma matsutake extract, the amounts of reactive oxygen species were decreased to 50% and 77%, respectively, which were lower than that of the control group. However, in the test group treated with the green tea polysaccharide together with the Tricholoma matsutake extract, the level of reactive oxygen species induced by the cigarette sample was significantly decreased to 22%. This suggests that treatment of cells with the reactive ingredients in combination leads to a greater decrease in the level of reactive oxygen species than treatment with the reactive ingredients alone.

Accordingly, the inventive composition containing the green tea polysaccharide together with the Tricholoma matsutake extract can effectively prevent skin aging and oxidation by reducing the level of reactive oxygen species induced by external harmful environments.

Test Example 2

Inhibitory Effects of Green Tea Polysaccharide and Tricholoma matsutake Extract on Expression of Pollution Antenna Protein (Aryl Hydrocarbon Receptor, AhR) Caused by Automobile Exhaust Gas 2-1: Preparation of Automobile Exhaust Gas Sample Exhaust soot stuck to the exhaust pipe of a diesel car were collected with a cotton swab, and only the cotton portion of the swab cotton, which was smeared with the soot, was extracted in DMSO for 13 hours. Next, the extracted portion was vortexed for 10 minutes, and the cotton was removed, thus obtaining an automobile exhaust gas sample.

2-2: Examination of Inhibition of AhR Expression

Fibroblasts were seeded into DMEM medium (containing 5% fetal bovine serum (FBS) and 100 IU penicillin G) in an 8-well chamber slide at a density of 5,000 cells/well. The next day, each well was replaced with FBS-free and phenol red-free DMEM medium, and after 24 hours, each well was treated with each of the samples shown in Table 2 below. For a negative control group, each well was treated only with soot/exhaust gas, and for a control group, each well was treated with 0.1% DMSO. For test groups, each well was treated with 200 ppm of the automobile exhaust gas sample, one or both of 50 ppm of the green tea polysaccharide and 10 ppm of the Tricholoma matsutake extract, and then incubated at 37° C.; for 2 days. The treated cells were analyzed by immunofluorescence (IF). Each well was washed with PBS containing 1 mM $CaCl_2$ and 1 mM $MgCl_2$. The cells were fixed with 3.5% paraformaldehyde at room temperature for 10 minutes. The fixed cells were washed three times with PBS for 10 minutes. The cells were treated with 0.1% Triton-100 for 5 minutes and washed three times with PBS for 10 minutes. AhR antibody (Santa Cruz), diluted in 0.05% Tween 20-containing PBS (PEST) at 1:250, was used as a primary antibody, and the cells were allowed to react with the primary antibody at 4° C. Then, the cells were washed three times with PBST for 10 minutes, and allowed to react with Rhodamine-conjugated secondary antibody (diluted at 1:400) at room temperature for 1 hour. Then, the cells were washed three times with PBST for 10 minutes. To stain the nuclei, the cells were stained with DAPI for about 3 minutes, and washed three times with PBST. Then, mounting solution was added, and the slide was covered with a cover glass. The stained slide was photographed by confocal microscopy (Ziess), and the results are shown in FIG. 1. Based on the photographed images, the expression of the pollution antenna (AhR) protein was quantified using Axiovert 4.7 program. The expression level of the AhR protein in the control group was set at 100%, and ratios relative to the control group were calculated. The calculation results are shown in Table 2 below.

TABLE 2

| Samples | Expression Ratio of AhR (%) |
|---|---|
| Control Group | 100 |
| Soot/Exhaust Gas | 157 |
| Green Tea Polysaccharide + Soot/Exhaust Gas | 129 |
| Tricholoma Matsutake Extract + Soot/Exhaust Gas | 137 |
| Green Tea Polysaccharide + Tricholoma Matsutake Extract + Soot/Exhaust Gas | 99 |

As can be seen in FIG. 1, in the groups treated with each of the green tea polysaccharide and the Tricholoma matsutake extract, the expression of AhR was somewhat decreased, but in the group treated with both the green tea polysaccharide and the Tricholoma matsutake extract, the expression of AhR could be inhibited to a level similar to that in the control group not treated with soot/exhaust gas.

As can be seen from the results in Table 2, the soot/exhaust gas increased the expression of AhR by 157% compared to the control group, suggesting that the soot/exhaust gas moved the pollution antenna protein (AhR) into the keratinocyte nuclei and increased the expression of AhR in the keratinocytes. In the groups treated with each of the green tea polysaccharide and the Tricholoma matsutake extract, the expression levels of the pollutant antenna protein could be somewhat to 129% and 137%, but in the group treated with both the green tea polysaccharide and the Tricholoma matsutake extract, the movement of the pollution antenna protein could be inhibited while the expression level thereof could be decreased to that in the control group.

Accordingly, the inventive cosmetic composition containing both the green tea polysaccharide and the Tricholoma matsutake extract can exhibit an excellent skin anti-aging effect and protect the skin from external harmful environments by inhibiting the expression of the pollution antenna AhR which is activated when various pollution factors transmit a harmful signal into the skin.

Test Example 3

Anti-Inflammatory Effects of Green Tea Polysaccharide and Tricholoma matsutake Extract 3-1: Examination of Inhibition of Prostaglandin E2 (PGE2) Production Fibroblasts were seeded into DMEM medium (containing 5% fetal bovine serum (FBS) and 100 IU penicillin G) in a 24-well plate at a density of $10^4$ cells/well. The next day, each well was replaced with FES-free and phenol red-free DMEM medium, and after 24 hours, each well as treated with each of the samples shown in Table 3 below. For a negative control group, each well was treated only with soot/exhaust gas, and for a control group, each well was treated with 0.1% DMSO. For test groups, each well was treated with 400 ppm of the automobile exhaust gas sample, one or both of 50 ppm of the green tea polysaccharide and 10 ppm of the *Tricholoma matsutake* extract, and then incubated at 37☐ for 2 days. The resulting cell cultures were harvested, and the level of PGE2 in the cell cultures was measured using a PGE2 ELISA kit (KGE004, R&D Systems). The production of PGE2 in the control group was set at 100%, and ratios relative to that in the control group were calculated. The calculation results are shown in Table 3 below.

TABLE 3

| Samples | Generation Ratio of PGE2 (Inflammation-Inducing Factor) (%) |
|---|---|
| Control Group | 100 |
| Soot/Exhaust Gas | 185 |
| Green Tea Polysaccharide + Soot/Exhaust Gas | 115 |
| *Tricholoma Matsutake* Extract + Soot/Exhaust Gas | 135 |
| Green Tea Polysaccharide + *Tricholoma Matsutake* Extract + Soot/Exhaust Gas | 67 |

As can be seen from the results in Table 3 above, the level of PGE2 which was increased to 185% by the automobile exhaust gas was decreased to 115% or 135% by treatment with each of the green tea polysaccharide and the *Tricholoma matsutake* extract. In the group treated with both the green tea polysaccharide and the *Tricholoma matsutake* extract, the level of the inflammation-inducing factor PGE2 was 67% which was lower than that in the control group. This suggests that the green tea polysaccharide and the *Tricholoma matsutake* extract have synergistic anti-inflammatory effects.

Accordingly, the cosmetic composition containing both the green tea polysaccharide and the *Tricholoma matsutake* extract shows an excellent anti-inflammatory effect by inhibiting the expression of the inflammatory factor PGE2 in the skin.

What is claimed is:

1. A method of inhibiting inflammation and oxidation of skin comprising topically applying to the skin a cosmetic composition which contains, as active ingredients, green tea polysaccharide and an aqueous *Tricholoma matsutake* extract in a ratio of 1.0:10.0 to 10.0:1.0 in the cosmetic composition.

2. The method of claim 1, wherein the green tea polysaccharide and the *Tricholoma matsutake* extract are present in a ratio of 1:2 to 5:1 in the cosmetic composition.

3. The method of claim 1, wherein each of the green tea polysaccharide and the *Tricholoma matsutake* extract are present in an amount of 0.01-20.0 wt % based on the total weight of the composition.

4. A method of promoting the health of skin tissue comprising topically applying to the skin a cosmetic composition which contains, as active ingredients, green tea polysaccharide and an aqueous *Tricholoma matsutake* extract in a ratio of 1.0:10.0 to 10.0:1.0 in the cosmetic composition.

5. The method of claim 4, wherein the green tea polysaccharide and the *Tricholoma matsutake* extract are present in a ratio of 1:2 to 5:1 in the cosmetic composition.

6. The method of claim 4, wherein each of the green tea polysaccharide and the *Tricholoma matsutake* extract are present in an amount of 0.01-20.0 wt % based on the total weight of the composition.

7. A method of combating loss of skin elasticity comprising topically applying to the skin a cosmetic composition which contains, as active ingredients, green tea polysaccharide and an aqueous *Tricholoma matsutake* extract in a ratio of 1.0:10.0 to 10.0:1.0 in the cosmetic composition.

8. The method of claim 7, wherein the green tea polysaccharide and the *Tricholoma matsutake* extract are present in a ratio of 1:2 to 5:1 in the cosmetic composition.

9. The method of claim 7, wherein each of the green tea polysaccharide and the *Tricholoma matsutake* extract are present in an amount of 0.01-20.0 wt % based on the total weight of the composition.

10. A method of protecting skin from external harmful environments comprising topically applying to the skin a cosmetic composition which contains, as active ingredients, green tea polysaccharide and an aqueous *Tricholoma matsutake* extract in a ratio of 1.0:10.0 to 10.0:1.0 in the cosmetic composition.

11. The method of claim 10, wherein the green tea polysaccharide and the *Tricholoma matsutake* extract are present in a ratio of 1:2 to 5:1 in the cosmetic composition.

12. The method of claim 10, wherein each of the green tea polysaccharide and the *Tricholoma matsutake* extract are present in an amount of 0.01-20.0 wt % based on the total weight of the composition.

* * * * *